(12) United States Patent
Zhang

(10) Patent No.: US 10,557,784 B2
(45) Date of Patent: Feb. 11, 2020

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 530 days.

(21) Appl. No.: 14/947,853

(22) Filed: Nov. 20, 2015

(65) Prior Publication Data

US 2017/0146440 A1 May 25, 2017

(51) Int. Cl.
*G01N 15/06* (2006.01)
*G01N 27/04* (2006.01)

(52) U.S. Cl.
CPC ..... *G01N 15/0656* (2013.01); *G01N 15/0606* (2013.01); *G01N 27/045* (2013.01)

(58) Field of Classification Search
CPC .......... G01N 15/0606; G01N 15/0656; G01N 27/045; G01N 15/06; G01N 27/04
See application file for complete search history.

(56) References Cited

U.S. PATENT DOCUMENTS

| | | | |
|---|---|---|---|
| 6,152,988 A * | 11/2000 | Plaks | ...................... B03C 3/155 55/341.1 |
| 6,634,210 B1 | 10/2003 | Bosch et al. | |
| 8,341,936 B2 | 1/2013 | Zhang | |
| 2002/0108889 A1 * | 8/2002 | Fujii | ...................... B01D 57/02 209/39 |
| 2010/0043527 A1 * | 2/2010 | Marra | .................... B60H 1/008 73/28.02 |
| 2011/0203348 A1 * | 8/2011 | Hedayat | ............. G01N 15/0656 73/23.33 |
| 2011/0315654 A1 * | 12/2011 | Vanhelmont | ............. H03H 3/04 216/13 |

(Continued)

FOREIGN PATENT DOCUMENTS

| | | |
|---|---|---|
| CN | 101208592 A | 6/2008 |
| CN | 101965511 A | 2/2011 |

(Continued)

OTHER PUBLICATIONS

Styles, Daniel Joseph et al., "Systems and Methods for Sensing Particulate Matter," U.S. Appl. No. 14/842,573, filed Sep. 1, 2015, 41 pages.

(Continued)

*Primary Examiner* — Alesa Allgood
*Assistant Examiner* — Brent J Andrews
(74) *Attorney, Agent, or Firm* — Geoffrey Brumbaugh; McCoy Russell LLP

(57) ABSTRACT

Methods and systems are provided for sensing particulate matter by a particulate matter (PM) sensor positioned downstream of a diesel particulate filter in an exhaust system. In one example, a PM sensor may include a pair of protruding interdigitated electrodes on a surface of the sensor and further include a plurality of flow guides also protruding from the surface of the sensor. By staggering the flow guides across the interdigitated electrodes, soot may be accumulated across multiple pathways and thereby, soot may be accumulated uniformly across the sensor surface.

14 Claims, 10 Drawing Sheets

(56) References Cited

U.S. PATENT DOCUMENTS

| | | | |
|---|---|---|---|
| 2013/0219990 A1 | 8/2013 | Allmendinger et al. | |
| 2014/0245815 A1* | 9/2014 | Nishijima | G01N 15/0656 |
| | | | 73/23.31 |
| 2015/0355066 A1 | 12/2015 | Zhang | |
| 2015/0355067 A1 | 12/2015 | Zhang et al. | |

FOREIGN PATENT DOCUMENTS

| | | |
|---|---|---|
| CN | 102939447 A | 2/2013 |
| CN | 103380282 A | 10/2013 |
| CN | 103782162 A | 5/2014 |

OTHER PUBLICATIONS

Zhang, Xiaogang, "System for Sensing Particulate Matter," U.S. Appl. No. 14/852,338, filed Sep. 11, 2015, 47 pages.
National Intellectual Property Administration of the People's Republic of China, Office Action and Search Report Issued in Application No. 201611013551.7, dated Dec. 12, 2019, 13 pages. (Submitted with Partial Translation).

* cited by examiner

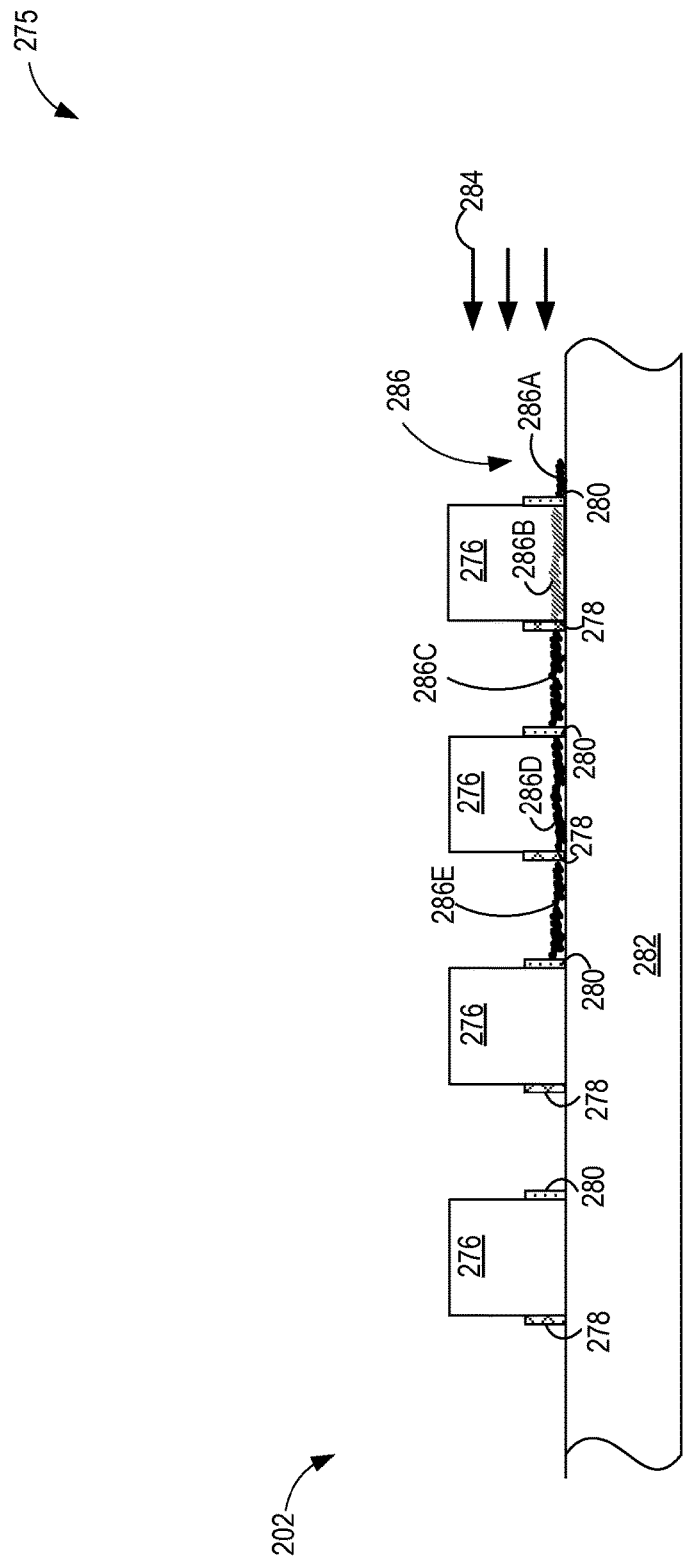

METHOD AND SYSTEM FOR EXHAUST PARTICULATE MATTER SENSING

FIELD

The present description relates generally to the design and use of resistive-type particle matter (PM) sensors in an exhaust gas flow.

BACKGROUND/SUMMARY

Diesel combustion may generate emissions, including particulate matter (PM). The particulate matter may include diesel soot and aerosols such as ash particulates, metallic abrasion particles, sulfates, and silicates. When released into the atmosphere, PM can take the form of individual particles or chain aggregates, with most in the invisible sub-micrometer range of 100 nanometers. Various technologies have been developed for identifying and filtering out exhaust PMs before the exhaust is released to the atmosphere.

As an example, soot sensors, also known as PM sensors, may be used in vehicles having internal combustion engines. A PM sensor may be located upstream and/or downstream of a diesel particulate filter (DPF), and may be used to sense PM loading on the filter and diagnose operation of the DPF. Typically, the PM sensor may sense a particulate matter or soot load based on a correlation between a measured change in electrical conductivity (or resistivity) between a pair of thin electrodes placed on a planar substrate surface of the sensor with the amount of PM deposited between the measuring electrodes. Specifically, the measured conductivity provides a measure of soot accumulation.

However, in such PM sensors, only a small fraction of the PM in the incoming exhaust gets collected across the electrodes formed on the surface of the sensor, thereby leading to low sensitivity of the sensors. Further, even the fraction of the PM that is accumulated on the surface may not be uniform due to a bias in flow distribution across the surface of the sensor. The non-uniform deposition of the PM on the sensor surface may further exacerbate the issue of low sensitivity of the sensor.

The inventors have recognized the above issues and identified an approach to at least partly address the issues. In one example, the issues above may be address by a particulate matter sensor comprising a pair of planar interdigitated electrodes spaced at a distance from each other and protruding from a surface of the PM sensor and a plurality of protruding flow guides located between the pair of planar interdigitated electrodes. Herein, the flow guides may include evenly spaced blocks arranged between pairs of tines of the interdigitated electrodes, spacing between the blocks being smaller than a distance between the pairs of tines of the pair of planar interdigitated electrodes. In this way, by including protruding electrodes and further including flow guides in between the electrodes, a single soot bridge may be divided into multiple soot bridges thereby increasing surface area coverage of the PM on the sensor surface and generating uniform distribution of the soot bridges on the sensor surface.

As one example, when a soot bridge formed between the electrodes encounters a flow guide, the soot bridge may branch out avoiding the block, and generating two pathways for the soot bridge to continue to form and grow. In this way, by branching the soot bridges at each of the flow guides, soot bridges may be able to grow across a larger surface area of the sensor, and may further generate a uniform distribution of soot on the sensor surface. Thus, by staggering the flow guides across the electrodes, soot bridges may be accumulated across multiple pathways and thereby, soot may be accumulated more uniformly across the sensor surface. Overall, these characteristics of the sensor may cause an output of the PM sensor to be more accurate, thereby increasing the accuracy of estimating particulate loading on a particulate filter.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2A-2D show magnified views of the PM sensor including protruding electrodes, and flow guides positioned there within.

DETAILED DESCRIPTION

Figure 1:
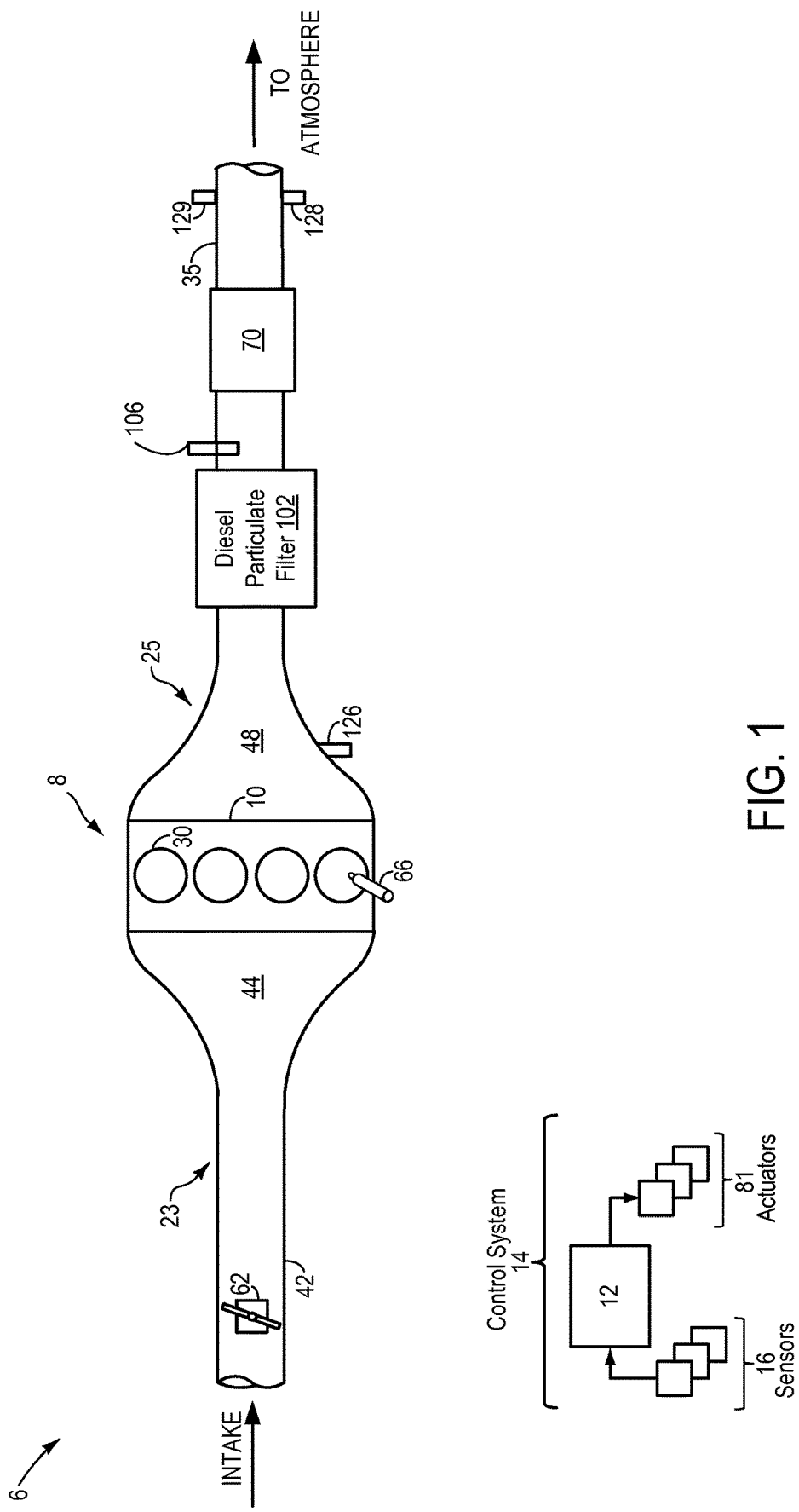
FIG. 1 shows a schematic diagram of an engine and an associated particulate matter (PM) sensor positioned in an exhaust flow.

The following description relates to systems and methods for sensing particulate matter (PM) in an exhaust flow of an engine system, such as the engine system shown in FIG. 1. A PM sensor placed in an exhaust passage of the engine system may include a pair of protruding interdigitated electrodes and further include a plurality of protruding flow guides located between alternate pairs of electrodes as shown in FIGS. 2A-2D. As such, the flow guides may include evenly spaced blocks arranged between pairs of electrodes. PM or soot entering the PM sensor may accumulate across the protruding electrodes (and not on the blocks, for example) forming PM streams or soot bridges. However, each block of the flow guide may block the soot bridge formation, and further divide the soot bridge into several pathways as shown in FIG. 3. A controller may be configured to perform a control routine, such as the routine of FIG. 4 to divide incoming PM streams into multiple PM streams at multiple flow guides positioned on the sensor surface. In addition, the controller may intermittently clean the PM sensor (as shown in the method presented at FIG. 5) to enable continued PM detection and perform diagnostics on a particulate filter positioned upstream of the PM sensor based on an output of the PM sensor (as shown in the method presented at FIG. 6). An example relation between a soot load of the PM sensor, a total length of the soot bridges and soot load on the particulate filter is shown in FIG. 7. In this way, by dividing the soot bridges at each block, soot bridges may be formed on a larger surface area of the sensor surface, and may further generate a uniform distribution of soot on the sensor surface. Overall, these characteristics of the sensor may cause an output of the PM sensor to be more accurate, thereby increasing the accuracy of estimating particulate loading on a particulate filter. In addition, by enabling more accurate diagnosis of the particulate filter, exhaust emissions compliance may be improved. As such, this reduces the high warranty costs of replacing functional particulate filters and exhaust emissions are improved and exhaust component life is extended.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIGS. 2A-2D, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. As yet another example, the actuators may include switches coupled to PM measurement circuitry. The control system 14 may include a controller 12. The controller 12 may be configured with computer readable instructions stored on non-transitory memory. The controller 12 receives signals from the various sensors of FIGS. 1, 2A-2D, and 3, processes the signals, and employs the various actuators of FIGS. 1, 2A-2D and 3 to adjust engine operation based on the received signals and instructions stored on a memory of the controller. Example routines are described herein with reference to FIGS. 4-6.

Figure 2A:
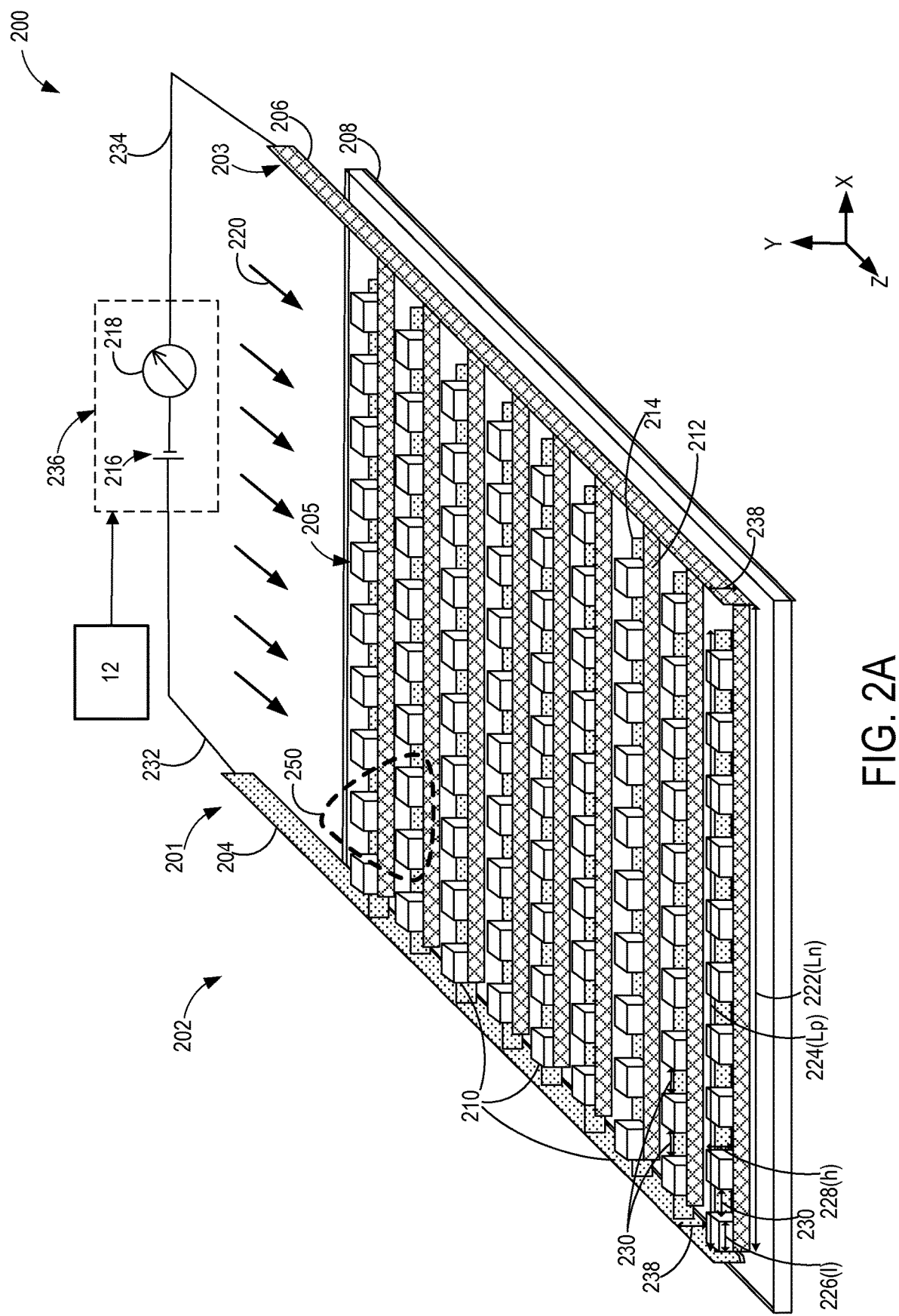
Figure 2B:
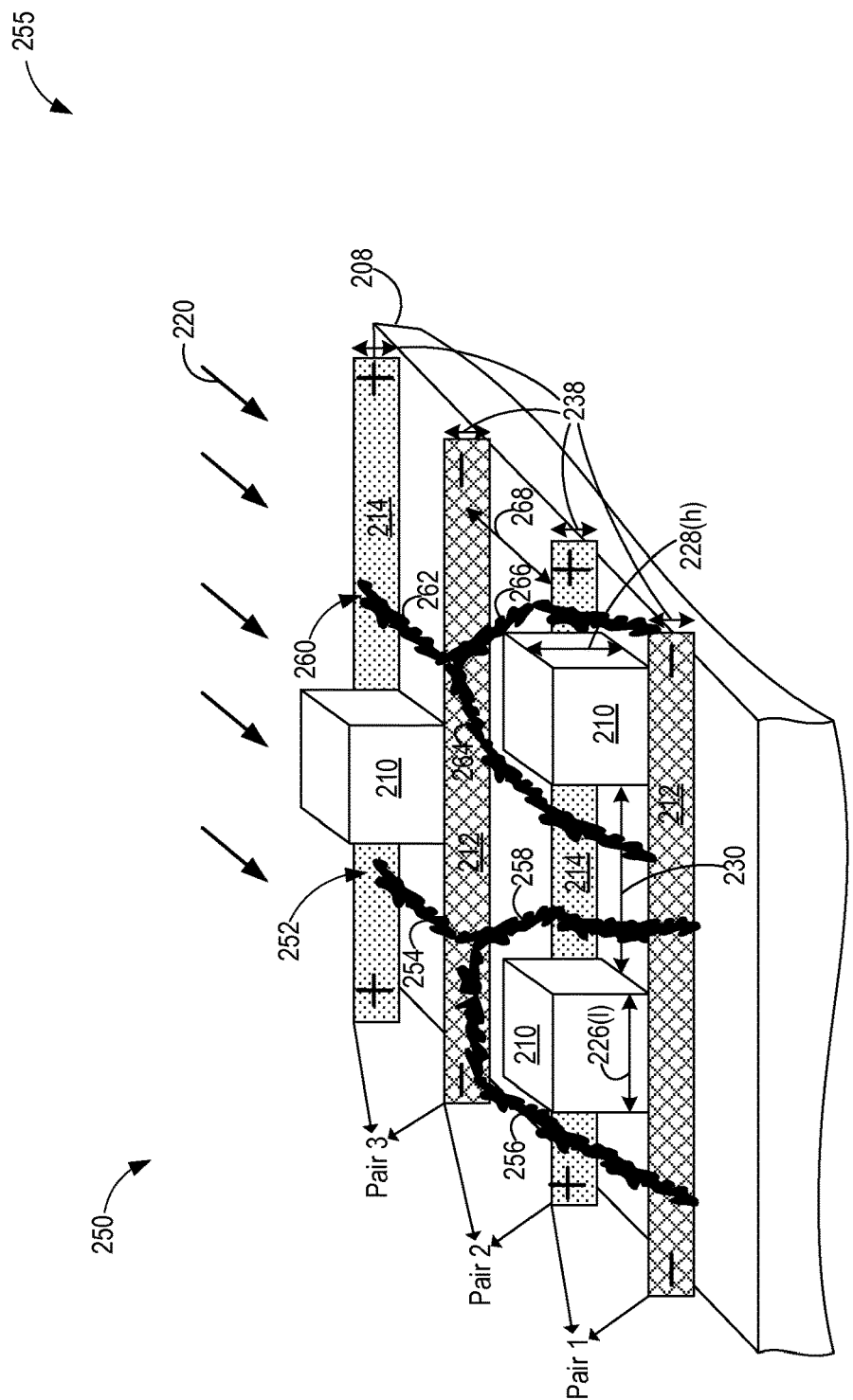
Figure 2D:
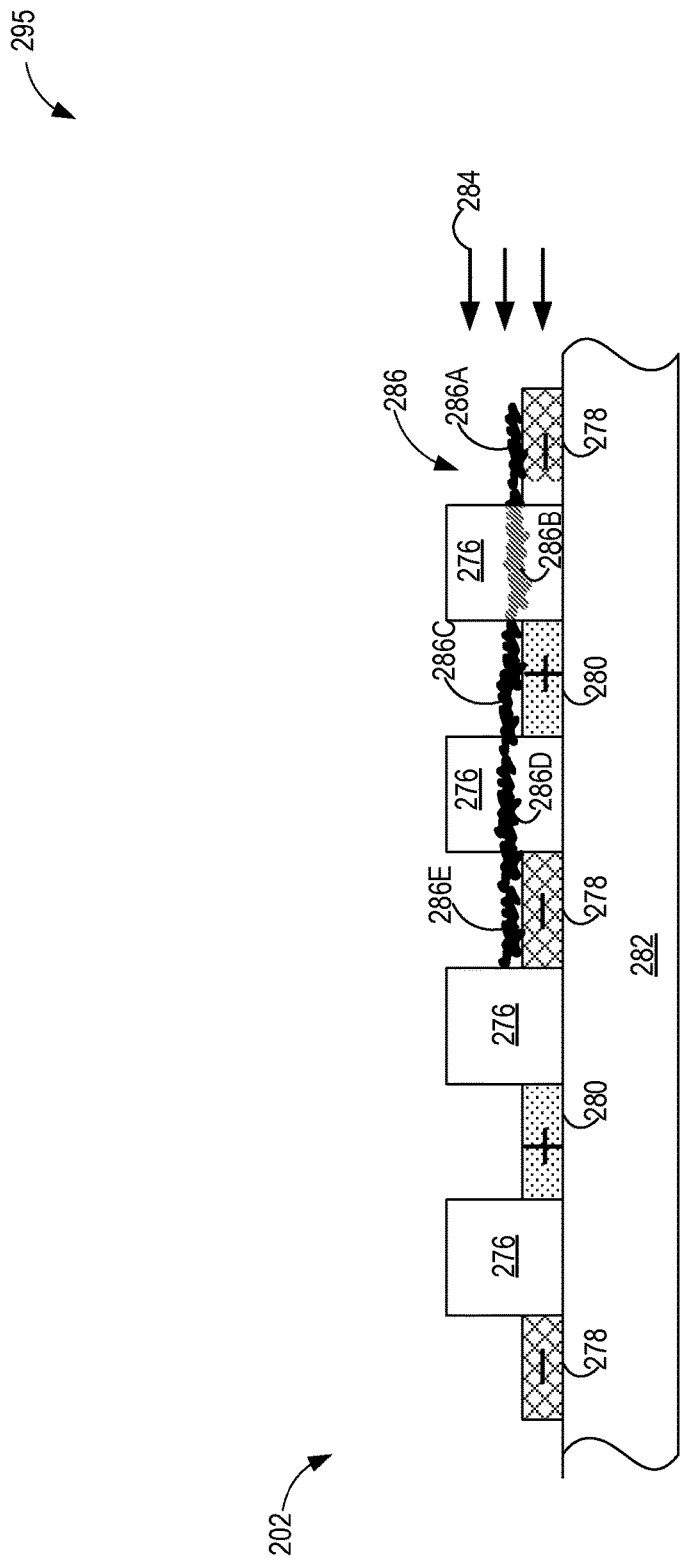
Figure 3:
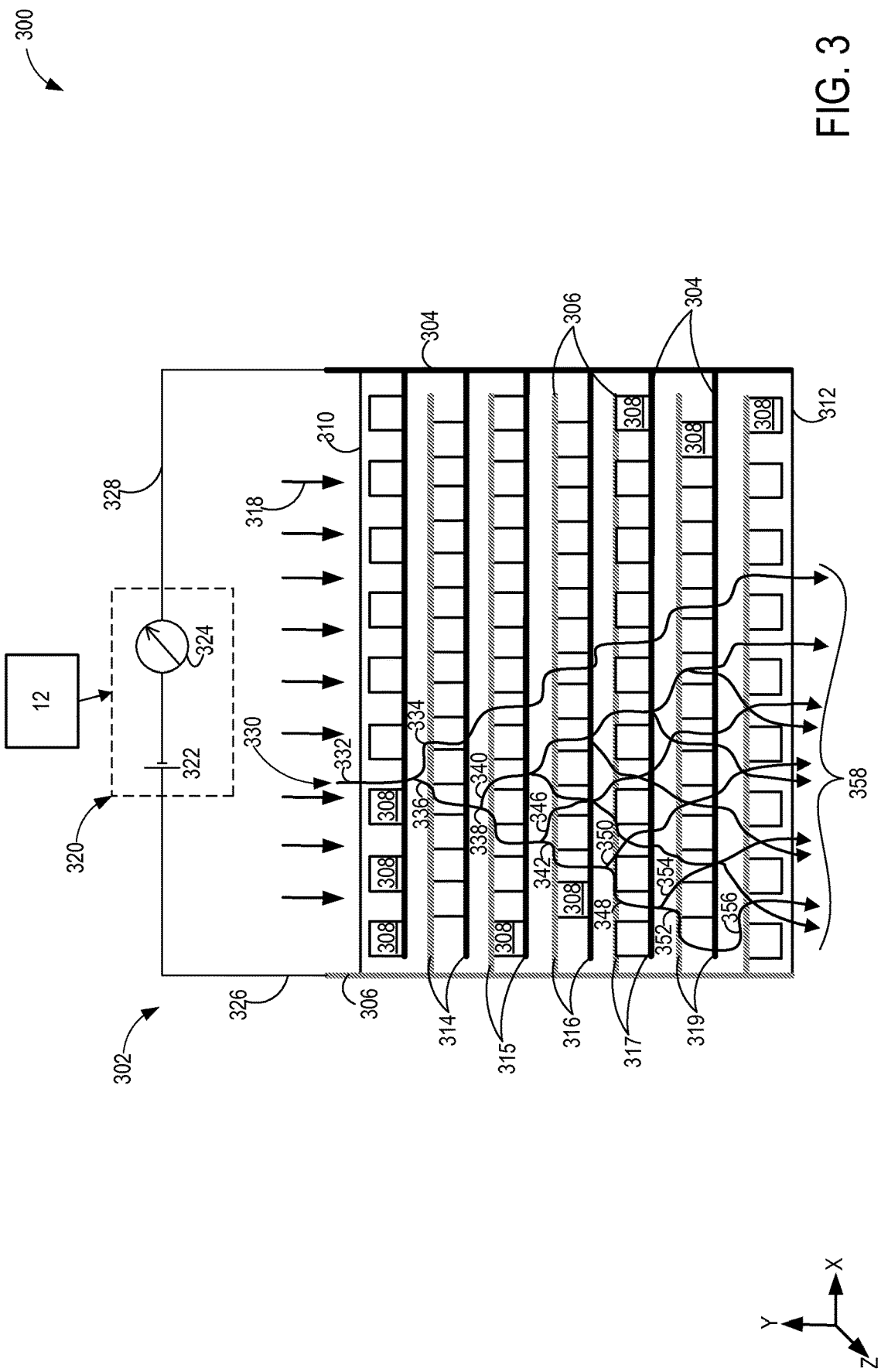
FIG. 3 shows multiple soot bridge pathways generated at each of the blocks of the flow guides.

Turning now to FIGS. 2A-2D, schematic views of an example embodiment of a particulate matter (PM) sensor 202 (such as PM sensor 106 of FIG. 1) are shown. Specifically, FIG. 2A shows a magnified view of the PM sensor including a pair of interdigitated electrodes protruding from sensor surface and further comprising a plurality of flow guides positioned there within. FIG. 2B shows a magnified view of a region 250 of PM sensor 202. FIG. 2C shows a side view of a portion of the PM sensor 202. FIG. 2D shows a side view of an alternate embodiment of the PM sensor 202. The PM sensor 202 may be configured to measure PM mass and/or concentration in the exhaust gas, and as such, may be coupled to an exhaust passage (e.g., such as the exhaust passage 35 shown in FIG. 1), upstream or downstream of a diesel particulate filter (such as DPF 102 shown in FIG. 1).

The PM sensor 202 may be a resistive-type PM sensor, and may be disposed inside an exhaust passage such that exhaust gases flow from downstream of a diesel particulate filter towards the PM sensor 202 as indicated by arrows 220. The PM sensor 202 may include a pair of planar continuous interdigitated electrodes 201 and 203 forming a "comb" structure spaced at a distance from each other. As such the PM sensor 202 may also include protection tube (not shown) covering the electrodes and further include conduits (not shown) within that direct the exhaust gases towards the electrodes as indicated by arrows 220. The electrodes 201 and 203 may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 201 and 203 are formed on a substrate 208 of the PM sensor 202 that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The interdigitated electrodes may further include plurality of "tines" 212 and 214, extending for a certain length into the sensor substrate 208 (along the X-axis). The spacing between the comb "tines" of the two electrodes may typically be in the range from 10 micrometers to 100 micrometers with the linewidth of each individual "tine" being about the same value, although the latter is not necessary. Herein, the pairs of tines of the interdigitated electrodes may be positioned orthogonal to the exhaust flow (arrows 220).

As such, the PM sensor substrate may include a heating element (not shown) and the PM sensor may be regenerated by heating the sensor substrate via the heating element to burn the accumulated soot particles from the surface of PM sensor 202. By intermittently regenerating the surface of PM sensor 202, it may be returned to a condition more suitable for collecting exhaust soot. In addition, accurate information pertaining to the exhaust soot level may be inferred from the sensor regeneration and relayed to the controller.

The PM sensor 202 including the interdigitated electrodes may be mounted on an exhaust tailpipe such that the sensing portion of the sensor that includes the interdigitated electrodes is extended inside the tailpipe to detect soot or PM in the incoming exhaust gases. The electrode 201 may be connected to a positive terminal of a voltage source 216 of an electric circuit 236 via a connecting wire 232. The electrode 201 may be connected to a measurement device 218 a connecting wire 234, and further connected to a negative terminal of the voltage source 216 of the electric circuit 236. Thus, each pair of tines are alternately connected to positive and negative terminal of the voltage source 216. The connecting wires 232 and 234, the voltage source 216 and the measurement device 218 are part of the electric circuit 236 and are housed outside the exhaust passage (as one example, <1 meter away). Further, the voltage source 216 and the measurement device 218 of the electric circuit 236 may be controlled by a controller, such as controller 12 of FIG. 1, so that particulate matter collected at the PM sensor may be used for diagnosing leaks in the DPF, for example. As such, the measurement device 218 may be any device capable of reading a resistance change across the electrodes, such as a voltmeter. As PM or soot particles get deposited between the electrodes, the resistance between the electrode pair may start to decrease, which is indicated by a decrease in the voltage measured by the measurement device 218. The controller 12 may be able to determine the resistance between the electrodes as a function of voltage measured by the measurement device 218 and infer a corresponding PM or soot load on the planar electrodes of the PM sensor 202. By monitoring the load on the PM sensor 202, the exhaust soot load downstream of the DPF may be determined, and thereby used to diagnose and monitor the health and functioning of the DPF. In some examples, the controller 12 may adjust the voltage source to supply a certain voltage to the electrodes of the PM sensors. When switches are disposed in the electric circuit, the controller 12 may determine the closing and opening of the switches based on a condition of the PM sensor. For example, when the PM sensor is collecting PM, the switches in the circuitry may be adjusted so that voltages are applied to the electrodes of the sensor. However, when the PM sensor is regenerating, the switches connecting the electrodes to the voltage source may be opened. Further, the heating circuit may be turned ON by the controller.

As such, the electrode 203 may include a planar non-interdigitated electrode portion 206 and further include several tines 212 contiguous with the electrode portion 206. Likewise, the electrode 201 may include a planar non-interdigitated electrode portion 204 and further include several tines 214 contiguous with the electrode portion 204. Herein, the tines 212 and the 214 are planar and interdigitated for a certain distance along the substrate 208 of the sensor forming a "comb" structure. The "comb" structure of the interdigitated electrodes may cover the portion of the planar substrate 208 which is exposed to the exhaust gases. Hereafter, the electrode 201 may be referred to as the positive electrode and may further include both the non-interdigitated electrode portion 204 and the interdigitated portion or tines 214. Similarly, the electrode 203 may be referred to as the negative electrode may further include both the non-interdigitated electrode portion 206 and the interdigitated portion or tines 212. The positive electrode and the negative planar interdigitated electrodes of the sensor may be spaced at a distance from one another and may protrude from the surface of the PM sensor, which will be explained in detail with reference to FIG. 2B.

The interdigitated portion of the negative electrode or tines 212 (nine tines shown as non-limiting example of the tines) extending for length $L_n$ into the sensor substrate 208, and is indicated by arrow 222, and further separated from the tines 214 by gap. Similarly, the tines 214 (nine tines shown as non-limiting example of the tines) may extend for a length $L_p$ into the sensor substrate 208, and is indicated by arrow 224. Further, the PM sensor 202 includes plurality of protruding flow guides 205 located between the pair of planar interdigitated electrodes. Herein, the flow guide 205 includes evenly spaced blocks 210 arranged between pairs of tines 212 and 214 of the interdigitated electrodes 201 and 203. Furthermore, the blocks 210 may be staggered between alternate pairs of tines 212 and 214 of the interdigitated electrodes. A region 250 of the PM sensor 202 is magnified in FIG. 2B for illustrative purpose. Herein, the blocks may be arranged between the tines such that the blocks are directly contacting or touching each of the tines 212 and 214. Further, the blocks as such may be separated from one another by a space with no other components there between. The blocks may be composed of material that is insulating, and not conducting.

Turning now to FIG. 2B, a magnified view 255 of region 250 of the PM sensor 202 is shown. Herein, a portion of the substrate 208 including portions of the tines 212 and 214 (four tines of alternating positive and negative voltages are shown) and three blocks 210 are shown. Exhaust gas flow into the region 250 is indicated by arrows 220. For illustrative purposes, the three pairs of positive and negative tines formed by four tines shown in FIG. 2B are marked as pair 1, pair 2 and pair 3.

As opposed to thin electrodes interdigitating electrodes that are typically used in PM sensors, both the positive electrode 201 and the negative electrode 203 of the PM sensor 202 may protrude from the sensor substrate 208 to a certain height as indicated by arrows 238. In some example embodiments, the height to which the positive electrode protrudes may be the same as the height to which the negative electrode protrudes from the surface of the sensor. In other examples, the protruding height may be different for the positive and the negative electrodes. Herein, the tines 212 and 214 of the electrodes are shown to protrude to a height (indicated by arrows 238) from the top surface of the substrate 208. The height (indicated by arrows 238) of the tines may be much smaller than the length ($L_p$ and $L_n$ shown in FIG. 2A) of the tines, for example. Further, the tines 212 and 214 may be separated by a distance shown by arrow 268. As described earlier, the spacing between the comb "tines" of the two electrodes may typically be in the range from 10 micrometers to 100 micrometers. The height of the tines may be much smaller than the spacing between the tines, for example.

As described earlier, the PM sensor 202 may include plurality of protruding flow guides 205 (as shown in FIG. 2A) located between the pair of planar interdigitated electrodes. The flow guide 205 includes evenly spaced blocks 210 arranged between pairs of tines 212 and 214 of the interdigitated electrodes 201 and 203 separated by a distance indicated by arrow 230. Herein, the spacing between the blocks (indicated by arrow 230) may be lower than a separation between the pairs of tines (indicated by arrow 268). Further, when disposed between tines of the interdigitated electrodes, the blocks 210 may touch both the tines. Thus, a width of the block may be equal to the spacing between the tines of the electrodes.

Each block 210 may be of a height h (indicated by arrow 228) and length l (indicated by arrow 226). The height h of each of the blocks may be larger than the height (indicated by arrow 238) of each of the pairs of tines of the interdigitated electrodes. In other words, the height of the blocks may be larger than the protrusion of the electrodes from the surface of the sensor, for example. In magnified view 255 of the region 250 of PM sensor 202, three blocks 210 are shown arranged between pairs of tines. Herein, two of the blocks 210 between pair 1 of the tines are separated by a distance (see arrow 230). Another single block 210 is positioned between pair 3 of the tines 212 and 214. Herein, no block is positioned between pair 2 of the tines. Thus, the blocks are staggered between alternate pairs of tines of the interdigitated electrodes. Furthermore, the block 210 positioned between pair 3 is positioned such that there is less than threshold overlap with the blocks positioned between pair 1, for example. In one example, the block between pair 3 is positioned in a region across pair 3 which overlaps with the spacing between blocks positioned in pair 1. In such an example, there is no overlap of the blocks positioned in pair 3 with the blocks positioned in pair 1. Thus, each alternate pair of tines include blocks arranged with less than threshold overlap with blocks in preceding alternating pairs of tines. Herein, pair 1 may be a preceding alternate pair to pair 3. In other examples, pair 3 may be a preceding alternate pair to pair 1. Thus, when the blocks are staggered along the PM sensor surface with such less than threshold overlap of blocks positioned along alternate pairs, there is room for the soot to grow and distribute uniformly around the blocks, for example.

The blocks 210 are arranged such that they are equally spaced from their nearest neighbors, for example. As such, the spacing between the blocks (indicated by arrow 230) may be smaller than a distance between the pairs of tines of the interdigitated electrodes (indicated by arrow 268). Herein, the width of the block 210 may be equal to the distance between the tines of the interdigitated electrodes.

Soot or PM in the exhaust gas is typically charged. Due electrostatic attraction between the charged PM and the interdigitated electrodes, PM get deposited on the electrodes and form soot bridges across the interdigitated electrodes. Two such example soot bridges 252 and 260 are shown in FIG. 2B. Herein, the tines 214 are connected to the positive terminal and hence held at a positive potential, and the tines 212 are connected to the negative terminal and hence held at a negative potential. The electric field generated between the interdigitated electrodes, specifically between the tines 212 and 214 allow soot or PM to get deposited on the electrodes. However, since the blocks are not connected to any voltage source, the soot does not grow on the blocks. The soot bridges may tend to avoid the blocks positioned between the pairs of tines and navigate towards the charged electrodes, for example. The soot bridge 252 begins to grow across pair 3 of the tines, and when it reaches pair 1, the soot bridge 252 bifurcates to avoid growing on the block. While avoiding the block, the soot bridge 252 forms two pathways and continues to grow across pair 1, for example. Similarly, soot bridge 260 begins to grow across pair 3 of the tines, and when it reaches pair 1, the soot bridge 260 bifurcates to avoid growing on the block. While avoiding the block, the soot bridge 260 forms two pathways and continues to grow across pair 1, for example.

Turning to FIG. 2C, a side view 275 of a portion of the PM sensor 202 of FIG. 2A is shown. Herein, equally spaced blocks 276 (such as blocks 210 of FIGS. 2A-2B) may be placed across alternate pairs of positive electrode 280 (such as positive electrode 201 of FIG. 1) and negative electrode 278 (such as negative electrode 203 of FIG. 1) protruding from a substrate 282 (such as substrate 208 of FIGS. 2A-2B). In the view 275, exhaust flow direction is indicated by arrows 284. As described earlier, soot bridges accumulate across the electrodes due to electrostatic attraction. For example, soot bridge 286 includes a soot bridge pathway 286A forming on the positive electrode 280. When the soot bridge pathway 286A encounters the block 276, the soot bridge may avoid the block 276 and continue to grow around the block 276, thereby generating soot bridge pathway 286B. As such, block is neutral with no voltage applied to it. Hence, the soot bridge may not feel any electrostatic force attracting it to or repelling to from the block. However, the soot bridge may experience an electrostatic pull from the negative electrode 276 positioned beyond the block. Thus, soot bridge continues to be formed along soot bridge pathway 286B behind the block 276 and reaches the negative electrode 278. The soot bride may not be able to climb over the block to reach the negative electrode 278 since the height of the block may be much larger than a length of the block, for example. Thus, the soot bridge bifurcates and grows around the block towards the negative electrode.

Once the soot bridge forms a pathway around the block towards the negative electrode 278, it may begin to feel an electrostatic pull from a succeeding positive electrode 280 positioned further along the substrate 282 at a distance from the negative electrode, for example. The soot bridge may continue to grow along pathway 286C towards the next positive electrode 280. The soot bridge may encounter another block 276. However, at block 276 the soot bridge pathway may bifurcate again, and soot bridge may continue to grow in front of the block, for example, along soot bridge pathway 286D until it reaches the negative electrode 278. Once at the negative electrode 278, the soot bridge continues to grow towards the next positive electrode 280 positioned at a distance from the negative electrode 278 along the soot bridge pathway 286E.

An alternate arrangement of the positive and the negative electrodes is shown in FIG. 2D. Turning to FIG. 2D, a side view 295 of a portion of the PM sensor 202 of FIG. 2A is shown. Herein, equally spaced blocks 276 (such as blocks 210 of FIGS. 2A-2B) may be placed across all pairs of positive electrode 280 (such as positive electrode 201 of FIG. 1) and negative electrode 278 (such as negative electrode 203 of FIG. 1) protruding from a substrate 282 (such as substrate 208 of FIGS. 2A-2B). Herein, the sensor is similar to the one shown in FIG. 2C, except that the positive and negative electrodes are only separated by the placement of blocks between them. Similar to FIG. 2C, exhaust flow direction is indicated by arrows 284. As described earlier, soot bridges accumulate across the electrodes due to electrostatic attraction. For example, soot bridge 286 includes a soot bridge pathway 286A formed on the negative electrode 278. When the soot bridge pathway 286A encounters the block 276, the soot bridge may avoid the block 276 and continue to grow around the block 276, thereby generating soot bridge pathway 286B. As such, block is neutral with no voltage applied to it. Hence, the soot bridge may not feel any electrostatic force attracting it to or repelling to from the block. However, the soot bridge may experience an electrostatic pull from the positive electrode 280 positioned beyond the block. Thus, soot bridge continues to be formed along soot bridge pathway 286B behind the block 276 and reaches the positive electrode 280. The soot bride may not be able to climb over the block to reach the positive electrode 280 since the height of the block may be much larger than a length of the block, for example. Thus, the soot bridge bifurcates and grows around the block towards the positive electrode.

Once at the positive electrode 280, the soot bridge continues to grow on the positive electrode 280 along the soot bridge pathway 286C. However, at block 276 the soot bridge pathway may bifurcate again, and soot bridge may continue to grow in front of the block, along soot bridge pathway 286D until it reaches the negative electrode 278. Once at the negative electrode 278, the soot bridge continues to grow on the negative electrode 278 along the soot bridge pathway 286E.

Figure 4:
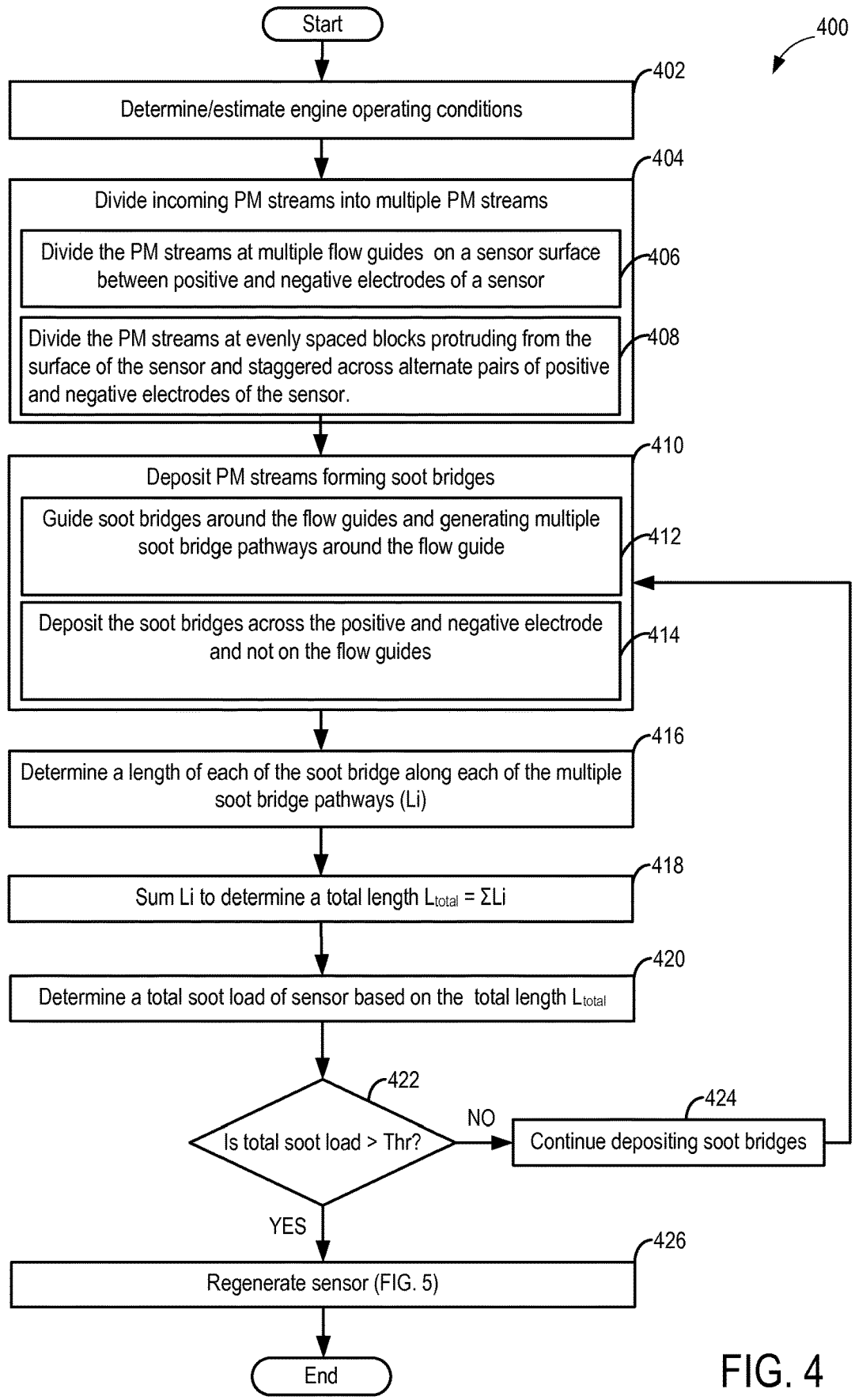
FIG. 4 shows a flow chart depicting a method for dividing incoming PM streams into multiple PM streams at multiple flow guides positioned on a surface of the PM sensor.

Further, the PM sensor may further including a controller (such as controller 12 of FIG. 1) with computer-readable instructions stored on non-transitory memory for dividing a single stream of PM in the exhaust flow into multiple streams of PM at each of the blocks located between the pairs of tines of the interdigitated electrodes, depositing the PM multiple streams of PM on the pairs of tines, and regenerating the PM sensor when a PM load between the pairs tines reaches a threshold PM load as explained in detail in FIGS. 3 and 4.

Thus, an example particulate matter (PM) sensor may include a pair of planar interdigitated electrodes spaced at a distance from each other and protruding from a surface of the PM sensor; and a plurality of protruding flow guides located between the pair of planar interdigitated electrodes. Additionally or alternatively, the flow guides of the PM sensor may include evenly spaced blocks arranged between pairs of tines of the interdigitated electrodes, spacing between the blocks being smaller than a distance between the pairs of tines of the pair of planar interdigitated electrodes. Additionally or alternatively, the blocks may be further staggered between alternate pairs of tines of the interdigitated electrodes. Additionally or alternatively, each alternate pair of tines may include blocks arranged with less than threshold overlap with blocks in preceding alternating pairs of tines. Additionally or alternatively, a spacing between the blocks between the pairs of tines is lower than a separation between the pairs of tines of the interdigitated electrodes. Additionally or alternatively, wherein a height of the blocks is larger than a height of each of the pairs of tines of the interdigitated electrodes. Additionally or alternatively, the pairs of tines of the interdigitated electrodes are positioned orthogonal to exhaust flow, and wherein each pair of tines are alternately connected to positive and negative terminal of a voltage source. Additionally or alternatively, wherein soot in the exhaust flow deposits between the pairs of tines of the interdigitated electrodes avoiding the blocks positioned between the pairs of tines. Additionally or alternatively, the PM sensor may further including a controller with computer-readable instructions stored on non-transitory memory for dividing a single stream of PM in the exhaust flow into multiple streams of PM at each of the blocks located between the pairs of tines of the interdigitated electrodes, depositing the PM multiple streams of PM on the pairs of tines, and regenerating the PM sensor when a PM load between the pairs tines reaches a threshold PM load.

The growth of the soot bridges across the PM sensor surface and the splitting of the soot bridge pathways may be analogous to balls dropping into a Galton board with pins staggered across the board, for example. Turning now to FIG. 3, a schematic top view 300 of the PM sensor with blocks staggered between the interdigitated electrodes of the PM sensor is shown. Herein, the arrangement of the blocks between alternate pairs of tines of the interdigitated electrodes may be similar to arrangement of pins in a Galton board.

The PM sensor 302 may be an example of PM sensor 202 described with reference to FIGS. 2A-2D. As such the details of the PM sensor 302 may be similar to the PM sensor 202 discussed earlier. Briefly, PM sensor 302 may include a pair of continuous interdigitated planar electrodes 304 and 306 separated by a gap formed on a sensor surface. The positive electrode 306 is connected to a positive terminal of a voltage source 322 via connecting wire 326 and the negative electrode 304 is connected to a measurement device 324 and a negative terminal of the voltage source 322 via connecting wire 328. A controller such as controller 12 of FIG. 1 may control the circuit 320 comprising of the voltage source 322 and the measurement device 324.

The PM sensor 302 may include an inlet 310 and an outlet 312 aligned orthogonal to the direction of flow of exhaust gas (indicated by arrows 318). The inlet 310 may guide exhaust gases from downstream of a particulate filter into the PM sensor, specifically, towards the sensing portion of the PM sensor 302 including the interdigitated electrodes and multiple flow guides. The outlet 312 may guide the exhaust gases out of the PM sensor 302 and into the tailpipe.

The PM sensor 302 may also include a plurality of uniformly spaced protrusions positioned in a staggered arrangement along the sensor surface. In one example, the protrusions may be blocks 308. Blocks 308 may be arranged across the PM sensor 302, specifically across the tines of the interdigitated electrodes and between alternate pairs of interdigitated electrodes. Herein, a height of each of the blocks may be greater than a height of each of the interdigitated electrodes. In addition, a length of each of the block may be smaller than a length of the each of the continuous interdigitated electrodes, specifically a length of the tines of the electrodes. Similar to the pins of the Galton board, the blocks 308 may be arranged in staggered order, and along alternate pairs of tines of the interdigitated electrodes. Herein, 314 and 315 indicate alternate pairs of the tines of the interdigitated electrodes 304 and 306. Similarly, 315 and 316 are alternate pairs, so are 316 and 317, and 317 and 319. Across the alternate pairs of the tines of interdigitated electrodes, the blocks 308 are staggered. Herein, blocks 308 placed across the pair 314 and the pair 315 may be positioned in such a way that the blocks across the pair 314 are aligned with the gaps formed between blocks 308 positioned across the pair 315. Similarly, blocks 308 placed across the pair 315 and the pair 316 may be positioned in such a way that the blocks across the pair 315 are aligned with the gaps formed between blocks 308 positioned across the pair 316. In the same way, blocks 308 placed across the pair 316 and the pair 317 may be positioned in such a way that the blocks across the pair 317 are aligned with the gaps formed between blocks 308 positioned across the pair 318. Likewise, blocks 308 placed across the pair 317 and the pair 319 may be positioned in such a way that the blocks across the pair 317 are aligned with the gaps formed between blocks 308 positioned across the pair 319. This arrangement of the blocks across alternate pairs of tines of the electrode may be similar to the arrangement of pins across the Galton board, for example. The PM sensor 302 may additionally or alternatively include a set of blocks arranged closer to the inlet 310 and another set of blocks arranged closer to the outlet 312 of the sensor.

Exhaust gases entering the PM sensor 302 may carry charged soot or PM. These charged soot or PM undergo electrostatic attraction towards the charged electrodes of the PM sensor and form soot bridges as explained earlier. Herein, a single stream of PM in the exhaust flow may be divided into multiple streams of PM at each of the blocks located between the pairs of tines of the interdigitated electrodes. Further, the PM streams may be deposited on the pairs of tines of the interdigitated electrodes. Further, soot or PM in the streams may accumulate across the pair of continuous interdigitated electrodes and not accumulate across the blocks, for example.

An example stream 330 is shown in the top view 300. Stream 330 may originate at the inlet 310 of the PM sensor 302, and get attracted to the negative electrode positioned close to the inlet forming a stream 332. Herein, the stream 332 may be formed in a space between the blocks. When the stream 332 reaches a block across the pair 314, the stream 332 may split into two streams 336 and 334 to avoid growing on the block and to reach the negative electrode of the pair 314, for example. Thus, a single stream 332 may be divided into two streams 336 and 334, thereby increasing the surface area for the soot to adhere. Similarly, stream 336 may spilt into streams 338 and 340 when encountering a block 308 across the pair 315. Likewise, when stream 338 reaches a block across the pair 316, the stream 338 may split into two streams 342 and 346 to avoid growing on the block and to reach the negative electrode of the pair 314. In a similar fashion, when the stream 342 reaches a block across the pair 317, the stream 342 may split into two streams 348 and 350 to avoid growing on the block and to reach the negative electrode of the pair 314, for example. Finally, the streams may exit the PM sensor 302 at the outlet 312 as indicated by arrows 358. As such, the streams may exit the PM sensor along the space between adjacent blocks positioned at the outlet of the PM sensor.

Figure 5:
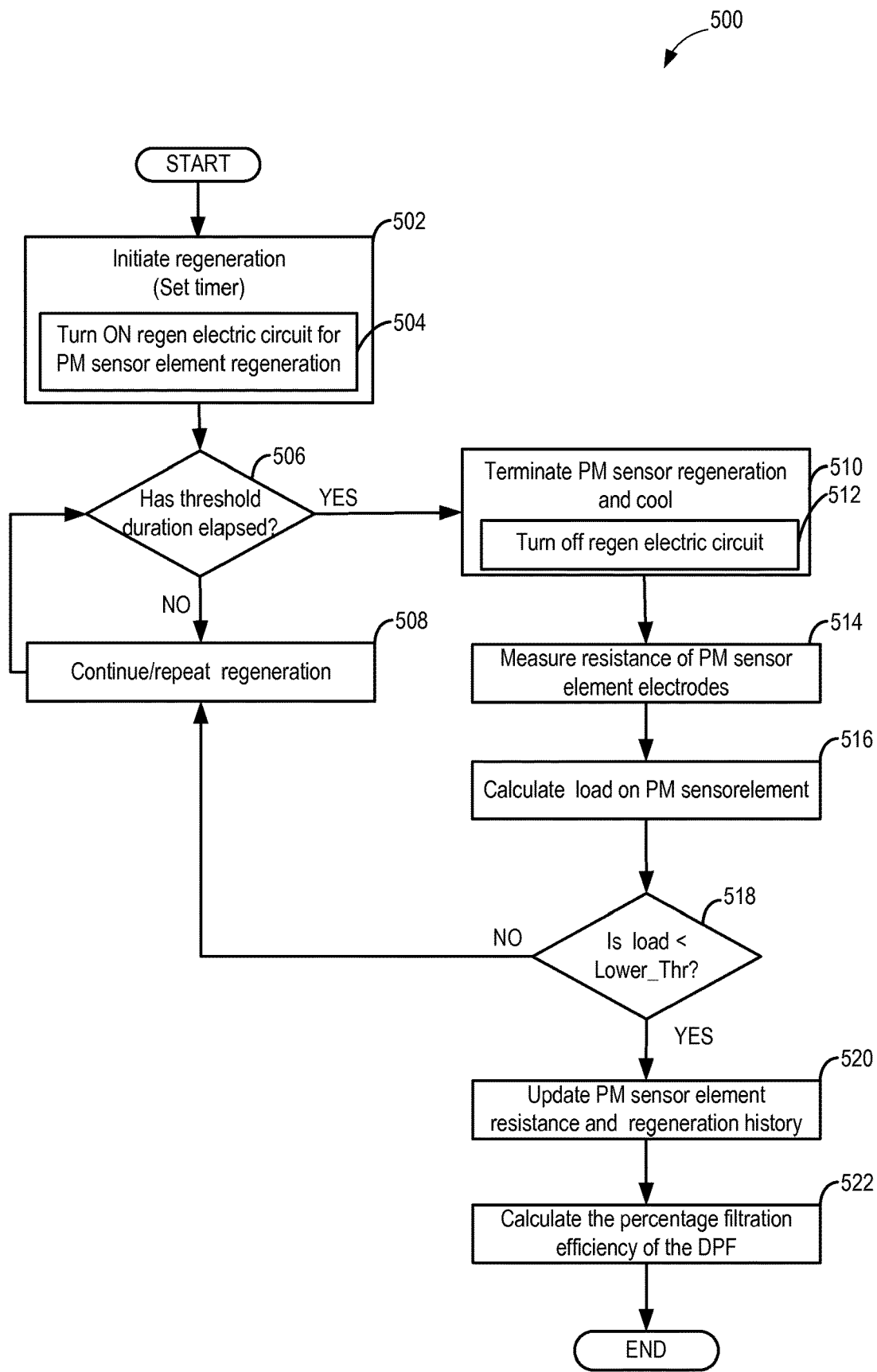
FIG. 5 shows a chart depicting a method for performing regeneration of the PM sensor.

Herein, the pathway of each of the stream may be a "random walk" and as the streams get spilt into multiple pathways, the surface area of adsorption of the soot onto the interdigitated electrodes increases. Further, similar to the Galton board, the soot bridges formed when splitting PM streams into multiple streams across the staggered blocks may lead to a uniform distribution of soot across the PM sensor electrode. In this way, by positioning blocks along the surface of the electrodes, soot bridges may be formed uniformly across the surface of the electrode. Further, soot loading and soot bridge building activity between the positive and negative electrodes may occur in shorter time frames. A controller, such as controller 12 of FIG. 1, may be able to determine a soot load on the PM sensor based on a sum total of soot accumulated across multiple pathways as explained with reference to FIG. 4. When the soot load of the PM sensor reaches a threshold, then the sensor may be regenerated as shown in FIG. 5. In this way, the PM sensor may detect PM exiting the particulate filter more accurately, and hence diagnose the DPF for leaks in a more reliable fashion.

Thus, an example particular matter (PM) sensor, may include a pair of continuous interdigitated electrodes formed on a sensor surface including a plurality of uniformly spaced protruding protrusions positioned in a staggered arrangement along the sensor surface, the protruding blocks positioned in between alternate pairs of the interdigitated electrodes. Additionally or alternatively, the protrusions may be blocks and a height of each of the blocks may be greater that a height of each of the interdigitated electrodes. Additionally or alternatively, a length of each of the blocks is smaller than a length of each of the interdigitated electrodes. Additionally or alternatively, the PM sensor may include a controller with computer-readable instructions stored on non-transitory memory for accumulating soot across the pair of continuous interdigitated electrodes and avoiding accumulating soot on the blocks, determining a soot load on the PM sensor based on a sum total of soot accumulated across the pair of interdigitated electrodes, and regenerating the PM sensor when the soot load is higher than a threshold.

Turning now to FIG. 4, illustrates a method 400 for dividing incoming PM streams into multiple PM streams at multiple flow guides positioned on a surface of the PM sensor. Specifically, the method determines soot load on the sensor based on a total length of soot bridges across the multiple PM streams. Instructions for carrying out method 400 and the rest of the methods included herein may be executed by a controller based on instructions stored on a memory of the controller and in conjunction with signals received from sensors of the engine system, such as the sensors described above with reference to FIGS. 1, 2A-2D and 3. The controller may employ engine actuators of the engine system to adjust engine operation, according to the methods described below.

At 402, method 400 includes determining engine operating conditions. Engine operating conditions determined may include, for example, engine speed, engine temperature, various exhaust air-fuel ratios, various exhaust temperatures, PM load on PM sensor, PM load on DPF, load on an exhaust LNT, ambient temperature, duration (or distance) elapsed since a last regeneration of PM sensor and DPF, etc.

Next, at 404, method 400 may divide incoming PM streams into multiple PM streams. Further, diving the incoming PM streams into multiple PM streams may include dividing the PM streams at multiple flow guides positioned on a surface of the PM sensor at 406, wherein the multiple flow guides are positioned between the positive and the negative electrode of the PM sensor. Herein, the flow guides may include evenly spaced blocks protruding from the surface of the sensor and further staggered across alternate pairs of the positive and negative electrodes of the sensor. Diving the PM streams into multiple PM streams may further include diving the PM streams at the evenly spaced blocks at 408. As such, the blocks are staggered across alternate pairs of the interdigitated electrodes, and further positioned such that there is less than threshold overlap of blocks with blocks in preceding alternating pairs of the electrodes. By placing the blocks in a staggered arrangement, PM stream may bifurcate whenever they encounter a block in their path, and further divide into multiple streams to avoid the block to find charged electrodes.

Next, at 410, the charged soot or PM in the PM streams may deposit across the electrodes forming soot bridges. Herein, depositing the soot bridges across the electrodes may further include guiding the soot bridges around the flow guides or blocks positioned across the electrodes, and further generating multiple soot bridge pathways around the flow guides at 412. Further, depositing the soot bridges may include depositing the soot bridges across the positive and negative electrode of the PM sensor and not on the flow guides at 414. Note that the actions of 404-414 describe actions occurring at the various locations and are not code programmed into the controller, in contrast to 402, and 416-426, for example.

Next, at 416, the method includes determining a length Li of each of the soot bridges along each of the multiple soot bridge pathways. As explained earlier, the soot bridges may form across multiple pathways. Herein, the multiple pathways are generated by positioning blocks along the interdigitated electrodes, for example. As the soot bridges grows across the electrodes, the length of the soot bridge may begin to increase. The controller may determine a length of each of the soot bridge formed across the surface of the sensor. The controller may determine the length of the soot bridges based on a current measured across the measurement device, for example.

Method 400 proceeds to 418 where a total length of the soot bridges is determined by summing Li of all the soot bridges formed on the surface of the sensor. Next, at 420 a total soot load on the PM sensor may be determined based on the total length of the soot bridges determined at 418. The controller may be able to determine the total soot load based on values stored in a look-up table for example. In some examples, the controller may be able to calculate the soot load based on the total length of the soot bridges.

Method 400 proceeds to 422 where it may be determined if the total soot load is higher than a threshold load, Thr. The threshold Thr, may be the threshold load that corresponds to PM sensor regeneration threshold. In some examples, the threshold Thr may be based on the PM load of the PM sensor above which the PM sensor may need to be regenerated. If the total soot load is lower than the threshold Thr, indicating that the PM sensor has not yet reached the threshold for regeneration, method 400 proceeds to 424, where the soot brides may be continued to be deposited across the electrodes, and the method returns to 410.

However if the total soot load is greater than the threshold Thr, then method proceeds to 426 where the PM sensor may be regenerated as described with reference to FIG. 5 and method ends. In this way, diagnostics on the DPF may be performed reliably and accurately by measuring and summing the length of soot bridges generated across the interdigitated electrodes.

Thus an example method includes A method for particulate matter (PM) sensing in an exhaust flow, comprising dividing incoming PM streams in the exhaust flow into multiple PM streams at multiple flow guides positioned on a sensor surface between positive electrodes and negative electrodes of a sensor, and depositing the PM streams across the positive electrodes and the negative electrodes forming soot bridges. Additionally or alternatively, the forming of the soot bridges may include depositing the soot bridges only across the positive electrodes and the negative electrodes, and not on the flow guides. Additionally or alternatively, the flow guides may comprise evenly spaced blocks protruding from the sensor surface of the sensor and staggered across alternate pairs of the positive electrodes and the negative electrodes of the sensor. Additionally or alternatively, a height of the blocks is higher than a height of each of the positive electrodes and the negative electrodes of the sensor. Additionally or alternatively, the dividing may further comprises guiding the soot bridges around the flow guides and generating multiple soot bridge pathways around the flow guides. Additionally or alternatively, the method may further comprise determining a length of each of the soot bridges along each of the multiple soot bridge pathways and summing the length to determine a total length. Additionally or alternatively, the method may further comprise determining a soot load of the sensor based on the total length and regenerating the sensor when the soot load of the sensor is higher than a threshold load.

Turning now to FIG. 5, a method 500 for regenerating the PM sensor (such as a PM sensor 106 shown at FIG. 1, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may need to be regenerated to enable further PM detection. At 502, regeneration of the PM sensor may be initiated and the PM sensor may be regenerated by heating up the sensor at 504. The PM sensor may be heated by actuating a heating element coupled thermally to the sensor electrode surface, such as a heating element embedded in the sensor, until the soot load of the sensor has been sufficiently reduced by oxidation of the carbon particles between the electrodes. The PM sensor regeneration is typically controlled by using timers and the timer may be set for a threshold duration at 502. Alternatively, the sensor regeneration may be controlled using a temperature measurement of the sensor tip, or by the control of power to the heater, or any or all of these. When timer is used for PM sensor regeneration, then method 500 includes checking if the threshold duration has elapsed at 506. If the threshold duration has not elapsed, then method 500 proceeds to 508 where the PM sensor regeneration may be continued. If threshold duration has elapsed, then method 500 proceeds to 510 where the soot sensor regeneration may be terminated and the electric circuit may be turned off at 512. Further, the sensor electrodes may be cooled to the exhaust temperature for example. Method 500 proceeds to 514 where the resistance between the electrodes of the PM sensor is measured. From the measured resistance, a soot bridge length may be determined, and further the PM or soot load of the PM sensor (i.e., the accumulated PMs or soot between the electrodes of the PM sensor) may be calculated at 516 and the method proceeds to 518. At 518, the calculated soot load of the PM sensor may be compared with a threshold, Lower_Thr. The threshold Lower_Thr, may be a lower threshold, lower than the regeneration threshold, for example, indicating that the electrodes are sufficiently clean of soot particles. In one example, the threshold may be a threshold below which regeneration may be terminated. If the soot load continues to be greater than Lower_Thr, indicating that further regeneration may be required, method 500 proceeds to 508 where PM sensor regeneration may be repeated. However, if the PM sensor continues to undergo repeated regenerations, the controller may set error codes to indicate that the PM sensor may be degraded or the heating element in the soot sensor may be degraded. If the soot load is lower than the threshold Lower_Thr, indicating that the electrode surface is clean, method 500 proceeds to 520, where the soot sensor resistance and regeneration history may be updated and stored in memory. For example, a frequency of PM sensor regeneration and/or an average duration between sensor regenerations may be updated. At 522, various models may then be used by the controller to calculate the percentage efficiency of the DPF the filtration of soot. In this way, the PM sensor may perform on-board diagnosis of the DPF.

Figure 6:
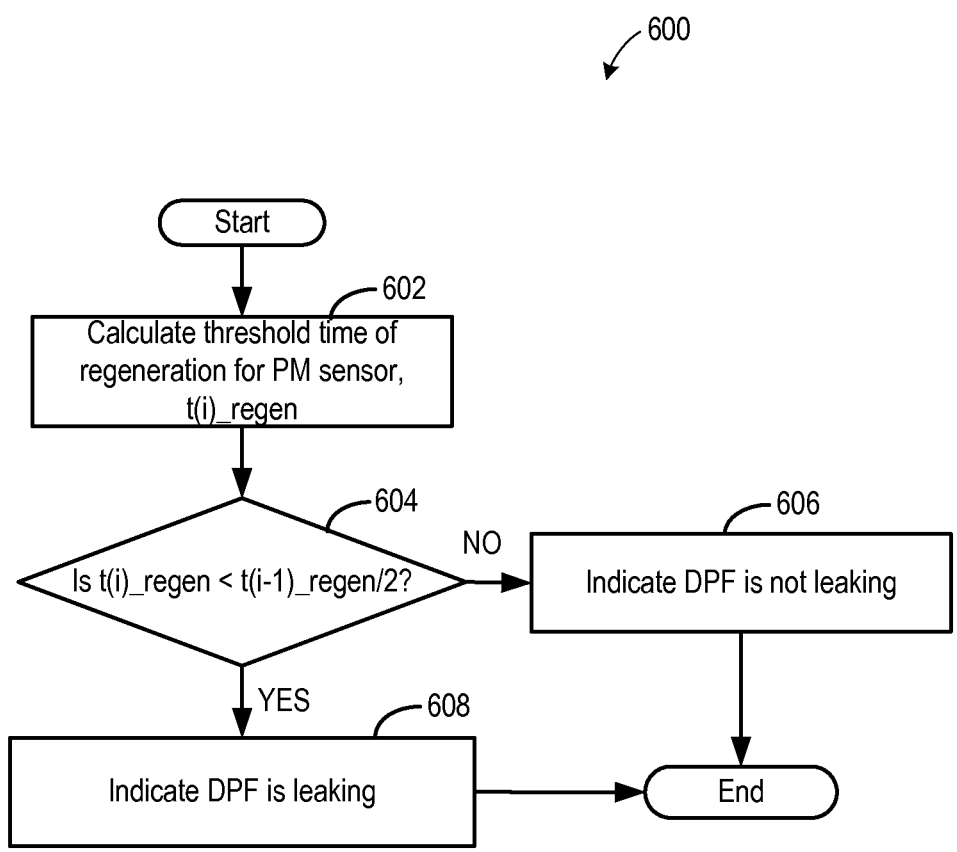
FIG. 6 shows a flow chart depicting a method for diagnosing leaks in a particulate filter positioned upstream of the PM sensor.
Figure 7:
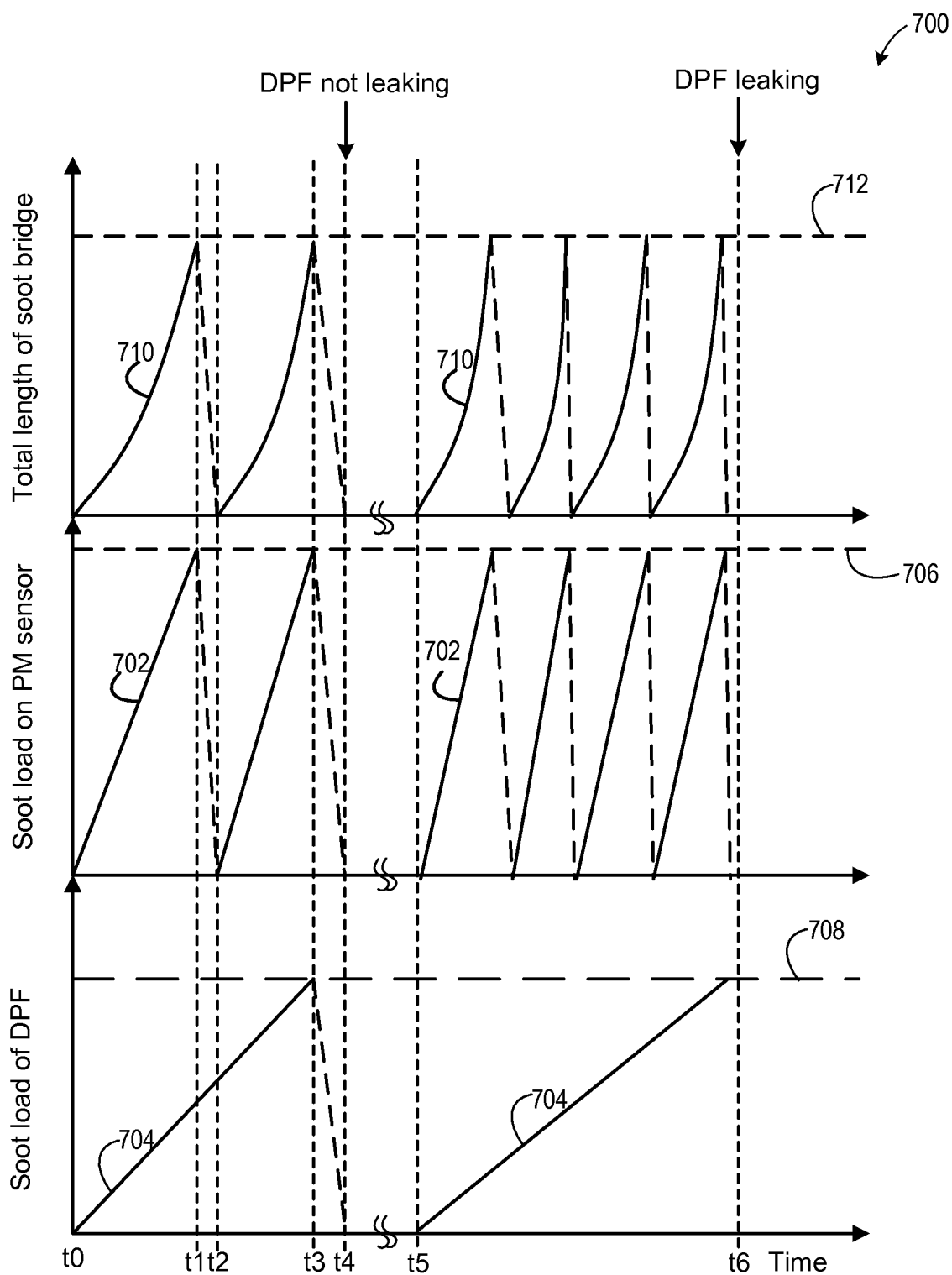
FIG. 7 shows an example relationship between a soot load of the PM sensor, a total length of the soot bridges and soot load on the particulate filter.

FIG. 6 illustrates an example routine 600 for diagnosing DPF function based on the regeneration time of the PM sensor. At 602, it may be calculated by the controller, through calibration, the time of regeneration for the PM sensor, t(i)_regen, which is the time measured from end of previous regeneration to the start of current regeneration of the PM sensor. At 604, compare t(i)_regen to t(i−1)_regen, which is the previously calibrated time of regeneration of the PM sensor. From this, it may be inferred that the soot sensor may need to cycle through regeneration multiple times in order to diagnose the DPF. If the t(i)_regen is less than half the value of t(i−1) region, then at 608 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code.

A current regeneration time of less than half of the previous regeneration time may indicate that the time for electric circuit to reach the R_regen threshold is shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change of regeneration time in the soot sensor does not reach threshold t_regen, then at 606 DPF leaking is not indicated. In this way, leaks in a particulate filter positioned upstream of the particulate matter sensor may be detected based on a rate of deposition of the particulates on the particulate matter sensor element.

Turning now to FIG. 7, map 700 shows an example relationship between total length of soot bridges, soot load on the PM sensor and the soot load on the particulate filter. Specifically, map 700 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and particulate filter.

The first plot from the top of FIG. 7 shows total length of soot bridge formed across the surface of the PM sensor. As previously described, when PM get deposited across the interdigitated electrodes, soot bridges may form across the electrodes. Furthermore, due to the multiple flow guides positioned across the electrodes, multiple soot bridge pathway may be generated, as a result of which the length of the soot bridge may continue to increase (plot 710). The controller may be able to determine a soot load (plot 702) based on the total length of the soot bridges. As such, the total length of the soot bridge and the soot load is at its lowest value at the bottom of the plots and increases in magnitude toward the top of the plot in the vertical direction. The horizontal direction represents time and time increases from the left to the right side of the plot. Horizontal marker 706 represents the threshold current for regeneration of the PM sensor in the top plot. Plot 704 represents the soot load on the DPF, and the horizontal marker 708 represents the threshold soot load of DPF in the second plot.

Between t0 and t1, a PM sensor regeneration cycle is shown. At time to, the PM sensor is in a relatively clean condition, as measured by low total PM sensor current. A controller coupled to the PM sensor determines a total length of the soot bridges by summing the length of each of the soot bridges formed across the multiple pathways, and further determines a soot load (702) of the PM sensor based on the total length of the soot bridges. When the controller determined the soot load to be small, it may send instructions to a regeneration circuit to end supplying heat, so that a detection circuit may begin detecting PM load accumulation. As PM load increases on the sensor, soot bridges begin to form and the length of the soot bridges begin to increase. Thus, the total length of the soot bridges that includes summing the length of each of the soot bridges generated across the electrode may also begin to increase (plot 710). The controller may determine the total soot load (plot 702) on the sensor based on the total length of the soot bridges (plot 710). Between t0 and t1, PM continues to accumulate and form soot bridges across multiple pathways and the total PM load (plot 702) increases accordingly and further soot load on DPF also increases (plot 704). In some examples, soot load on the DPF may be based on PM sensor load when PM sensor is located upstream of DPF, for example. The controller may be able to calculate distribution of the soot bridges and further determine length of the soot bridges by calculating the change in current or resistance across the electrodes, for example.

At t1, the PM sensor load (plot 702) reaches the threshold load for regeneration of the PM sensor (marker 706). The threshold load for regeneration may also be based on a threshold length of soot bridges (marker 712). At t1, PM sensor regeneration may be initiated as explained earlier. Thus, between t1 and t2, the PM sensor may be regenerated by turning on electric circuit for regeneration, for example. At t2, the PM sensor may be sufficiently cool, and may begin to accumulate PMs. Thus, between t2 and t3 (DPF regeneration cycle), the PM sensor may continue to accumulate PMs. During time between t2 and t3, DPF soot load continues to increase (plot 704). However, at t3, the soot load on the DPF (plot 604) reaches the threshold soot load for DPF regeneration (marker 708). Between t3 and t4, the DPF may be regenerated to burn off the soot deposited on the DPF as explained earlier. Further at t4, the PM sensor regeneration frequency may be compared with previous regeneration frequency of the PM sensor. Based on the PM sensor regeneration frequency remaining similar to previous cycles, the DPF maybe determined to be not leaking. In this way, based on PM sensor output, DPF may be monitored and diagnosed for leaks.

Between t5 and t6, another DPF cycle is shown. Herein, between t5 and t6, the soot load on the DPF gradually increases (plot 704). During this time, the total length of the soot bridges and the soot load on the PM sensor may be monitored. Plots 702 and 710 shows the PM sensor going through multiple regeneration cycles as described earlier. However, the frequency of regeneration of the PM sensor has nearly doubled (plot 702). As explained earlier, higher frequency of regeneration in the PM sensor may indicate that the outflowing exhaust gas is composed of a higher amount of particulate matter than realized with a normally functionally DPF, therefore at t6, DPF leak may be indicated.

In this way, a more accurate measure of the exhaust PM load, and thereby the DPF soot load can be determined. As such, this improves the efficiency of filter regeneration operations, and reduces the need for extensive algorithms. In addition, by enabling more accurate diagnosis of an exhaust DPF, exhaust emissions compliance may be improved. As such, this reduces the high warranty costs of replacing functional particulate filters and exhaust emissions are improved and exhaust component life is extended. In this way, by staggering plurality of blocks along the surface of the sensor, soot may be distributed across the surface of the sensor, and an accurate measure of the PM sensor loading may be determined. Further by using protruding electrodes on the surface of the sensor, soot loading and soot bridge formation may be increased. The technical effect of staggering blocks across the sensor surface, and between the interdigitated electrodes, is that multiple pathways for the soot bridge formation may be generated. By summing the soot bridge length across the multiple pathways and determining the soot load of the sensor, PM sensor may detect PM in the exhaust more accurately and hence diagnose the DPF for leaks in a more reliable fashion.

The systems and methods described above also provide for a particulate matter sensor, comprising a pair of planar interdigitated electrodes spaced at a distance from each other and protruding from a surface of the PM sensor, and a plurality of protruding flow guides located between the pair of planar interdigitated electrodes. In a first example of the particulate matter sensor, the sensor may additionally or alternatively include wherein the flow guides includes evenly spaced blocks arranged between pairs of tines of the interdigitated electrodes, spacing between the blocks being smaller than a distance between the pairs of tines of the pair of planar interdigitated electrodes. A second example of the PM sensor optionally includes the first example and further includes wherein the blocks are further staggered between alternate pairs of tines of the interdigitated electrodes. A third example of the PM sensor optionally includes one or more of the first and the second examples, and further includes wherein each alternate pair of tines include blocks arranged with less than threshold overlap with blocks in preceding alternating pairs of tines. A fourth example of the PM sensor optionally includes one or more of the first through the third examples, and further includes, wherein a spacing between the blocks between the pairs of tines is lower than a separation between the pairs of tines of the interdigitated electrodes. A fifth example of the PM sensor optionally includes one or more of the first through the fourth examples, and further includes, wherein a height of the blocks is larger than a height of each of the pairs of tines of the interdigitated electrodes. A sixth example of the PM sensor optionally includes one or more of the first through the fifth examples, and further includes wherein the pairs of tines of the interdigitated electrodes are positioned orthogonal to exhaust flow, and wherein each pair of tines are alternately connected to positive and negative terminal of a voltage source. A seventh example of the PM sensor optionally includes one or more of the first through the third examples, and further includes wherein soot in the exhaust flow deposits between the pairs of tines of the interdigitated electrodes avoiding the blocks positioned between the pairs of tines. An eighth example of the PM sensor optionally includes one or more of the first through the third examples, and further includes a controller with computer-readable instructions stored on non-transitory memory for dividing a single stream of PM in the exhaust flow into multiple streams of PM at each of the blocks located between the pairs of tines of the interdigitated electrodes, depositing the PM multiple streams of PM on the pairs of tines, and regenerating the PM sensor when a PM load between the pairs of tines reaches a threshold PM load.

The systems and methods described above also provide for a particulate matter sensor, comprising a pair of continuous interdigitated electrodes formed on a sensor surface including a plurality of uniformly spaced protruding blocks positioned in a staggered arrangement along the sensor surface, the protruding blocks positioned in between alternate pairs of the interdigitated electrodes. In a first example of the particulate matter sensor, the sensor may additionally or alternatively include wherein a height of each of the blocks is greater that a height of each of the interdigitated electrodes. A second example of the PM sensor optionally includes the first example and further includes wherein a length of each of the blocks is smaller than a length of each of the interdigitated electrodes. A third example of the PM sensor optionally includes one or more of the first and the second examples, and further includes a controller with computer-readable instructions stored on non-transitory memory for accumulating soot across the pair of continuous interdigitated electrodes and avoiding accumulating soot on the blocks, determining a soot load on the PM sensor based on a sum total of soot accumulated across the pair of interdigitated electrodes; and regenerating the PM sensor when the soot load is higher than a threshold.

The systems and methods described above also provide for a method of particulate matter sensing in an exhaust flow, comprising dividing incoming PM streams in the exhaust flow into multiple PM streams at multiple flow guides positioned on a sensor surface between positive electrodes and negative electrodes of a sensor, and depositing the PM streams across the positive electrodes and the negative electrodes forming soot bridges. In a first example of the method, the method may additionally or alternatively include wherein the forming of the soot bridges includes depositing the soot bridges only across the positive electrodes and the negative electrodes, and not on the flow guides. A second example of the method optionally includes the first example, and further includes wherein the flow guides comprise evenly spaced blocks protruding from the sensor surface of the sensor and staggered across alternate pairs of the positive electrodes and the negative electrodes of the sensor. A third example of the method optionally includes one or more of the first and the second examples, and further includes wherein a height of the blocks is higher than a height of the each of the positive electrodes and the negative electrodes of the sensor. A fourth example of the method optionally includes one or more of the first through the third examples, and further includes wherein the dividing further comprises guiding the soot bridges around the flow guides and generating multiple soot bridge pathways around the flow guides. A fifth example of the method optionally includes one or more of the first through the fourth examples, and further includes determining a length of each of the soot bridges along each of the multiple soot bridge pathways and summing the length to determine a total length. A sixth example of the method optionally includes one or more of the first through the fifth examples, and further comprising determining a soot load of the sensor based on the total length and regenerating the sensor when the soot load of the sensor is higher than a threshold load.

Note that the example control and estimation routines included herein can be used with various engine and/or vehicle system configurations. Selected actions of the control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter (PM) sensor, comprising:
a pair of continuous interdigitated electrodes formed on a sensor surface and including two planar, non-interdigitated electrode portions and a plurality of uniformly spaced protruding interdigitated electrode portions, each contiguous with and extending from one of the two planar, non-interdigitated electrode portions, positioned in a staggered arrangement along and directly on the sensor surface, where a plurality of blocks is positioned in between each alternate pair of the interdigitated electrode portions, wherein each of the plurality of blocks is separated from one another by a first space with no other components therebetween and composed of material that is not conducting, the first space arranged between adjacent blocks, the adjacent blocks arranged between a same alternate pair of the interdigitated electrode portions, and wherein each alternate pair of the interdigitated electrode portions is separated from one another by a second space with no components therebetween, the second space arranged between adjacent alternate pairs of the interdigitated electrode portions.

2. The PM sensor of claim 1, wherein a height of each of the blocks is greater than a height of each of the interdigitated electrode portions and wherein the first space defines a first distance between adjacent blocks, the first distance arranged parallel to a direction in which the pair of interdigitated electrode portions extends from one of the two planar, non-interdigitated electrode portions, and wherein the second space defines a second distance between adjacent alternate pairs of the interdigitated electrode portions, the second distance arranged perpendicular to the direction in which the plurality of interdigitated electrode portions extends from one of the two planar, non-interdigitated electrode portions.

3. The PM sensor of claim 2, wherein a length of each of the blocks is smaller than a length of each of the interdigitated electrode portions and wherein, for each alternate pair of interdigitated electrode portions, one interdigitated electrode portion of the alternate pair is contiguous with and extends from a first one of the two planar, non-interdigitated electrode portions toward a second one of the two planar, non-interdigitated electrode portions and another one interdigitated electrode portion of the alternate pair is contiguous with and extends from the second one of the two planar, non-interdigitated electrode portions toward the first one of the two planar, non-interdigitated electrode portions.

4. The PM sensor of claim 3, further including a controller with computer-readable instructions stored on non-transitory memory for:
accumulating soot across the pair of continuous interdigitated electrodes and avoiding accumulating soot on the plurality of blocks;
determining a soot load on the PM sensor based on a sum total of soot accumulated across the pair of interdigitated electrodes; and
regenerating the PM sensor when the soot load is higher than a threshold.

5. A method for particulate matter (PM) sensing in an exhaust flow, comprising:
dividing incoming PM streams in the exhaust flow into multiple PM streams at multiple uniformly spaced protruding flow guides positioned directly on a sensor surface between a pair of continuous interdigitated positive and negative electrodes of a sensor, the continuous interdigitated positive and negative electrodes including alternate pairs of interdigitated electrode portions extending between planar, non-interdigitated portions, wherein each alternate pair of interdigitated electrode portions is separated from one another by a first space with no components therebetween, the first space defines a first distance between adjacent alternate pairs of the interdigitated electrode portions perpendicular to a direction in which the pairs of interdigitated electrode portions extend from one of the two planar, non-interdigitated electrode portions, the flow guides being non-conductive and positioned in a staggered arrangement along the sensor surface and separated from one another by a second space with no other components therebetween and positioned in between the alternate pairs of the interdigitated electrode portions, the second space defined by a second distance between adjacent flow guides arranged between a same alternate pair of interdigitated electrode portions, the second distance arranged parallel to a direction in which the alternate pairs of interdigitated electrode portions extend between the planar, non-interdigitated portions; and
depositing the PM streams across the positive electrodes and the negative electrodes and forming soot bridges.

6. The method of claim 5, further comprising forming the soot bridges by depositing the soot bridges only across the positive electrodes and the negative electrodes, and not on the flow guides.

7. The method of claim 6, wherein the flow guides comprise evenly spaced blocks protruding from the sensor surface of the sensor and staggered across alternate pairs of the positive electrodes and the negative electrodes of the sensor.

8. The method of claim 7, wherein the first distance is greater than the second distance.

9. The method of claim 8, wherein the dividing further comprises guiding the soot bridges around the flow guides and generating multiple soot bridge pathways around the flow guides.

10. The method of claim 9, further comprising determining a length of each of the soot bridges along each of the multiple soot bridge pathways and summing the length to determine a total length.

11. The method of claim 10, further comprising determining a soot load of the sensor based on the total length and regenerating the sensor when the soot load of the sensor is higher than a threshold load.

12. The method of claim 5, wherein the flow guides are blocks, and wherein a height of each of the blocks is greater that a height of each of the interdigitated positive and negative electrodes and wherein the distance between adjacent blocks, between the same alternate pair of interdigitated electrode portions, is defined parallel to a length of each interdigitated electrode portion of the alternate pair, where a first length of a first interdigitated electrode portion of the same alternate pair extends from a first planar, non-interdigitated portion of the planar, non-interdigitated portions to a distance from a second planar, non-interdigitated portion of the planar, non-interdigitated portions and a second length of a second interdigitated electrode portion of the same alternate pair extends from the second planar, non-interdigitated portion to a distance from the first planar, non-interdigitated portion.

13. The method of claim 12, wherein a length of each of the blocks is smaller than a length of each of the interdigitated positive and negative electrodes.

14. The method of claim 13, wherein the sensor is coupled to a controller with computer-readable instructions stored on non-transitory memory for:
  accumulating soot across the pair of continuous interdigitated positive and negative electrodes and avoiding accumulating soot on the blocks;
  determining a soot load on the sensor based on a sum total of soot accumulated across the pair of interdigitated positive and negative electrodes; and
  regenerating the sensor when the soot load is higher than a threshold.

* * * * *